United States Patent [19]

Czernuszka et al.

[11] Patent Number: 5,508,267
[45] Date of Patent: Apr. 16, 1996

[54] BIOACTIVE MATERIAL

[75] Inventors: Jan T. Czernuszka, Oxford; Karen I. Clarke, Cheshire, both of England

[73] Assignee: Isis Innovation Limited, United Kingdom

[21] Appl. No.: 211,977

[22] PCT Filed: Oct. 22, 1992

[86] PCT No.: PCT/GB92/01943

§ 371 Date: Jun. 24, 1994

§ 102(e) Date: Jun. 24, 1994

[87] PCT Pub. No.: WO/93/07910

PCT Pub. Date: Apr. 29, 1993

[30] Foreign Application Priority Data

Oct. 22, 1991 [GB] United Kingdom ............. 9122329

[51] Int. Cl.$^6$ .................. C07K 14/78; C07K 101/02; A61K 38/39; B05D 7/02
[52] U.S. Cl. .................. 514/21; 514/12; 530/352; 530/356; 530/840; 424/484; 427/414
[58] Field of Search ................ 514/12, 21; 530/350, 530/352, 356, 840, 842; 424/443, 444, 447, 484; 604/48, 50; 427/403, 414, 430.1, 427; 428/473, 478.2

[56] References Cited

U.S. PATENT DOCUMENTS 4,563,350  1/1986  Nathan et al. ............... 424/549
5,171,574  12/1992  Kuberasampath et al. ....... 424/423

FOREIGN PATENT DOCUMENTS 0227627  7/1987  European Pat. Off. .
0302847  2/1989  European Pat. Off. .
2570606  3/1986  France .

OTHER PUBLICATIONS

Maier et al. "The Dynamics of Formation of a Collagen–Phosphophoryn Conjogate in Relation to Passage of the Mineralization Front in Rat Hicisor Dentin" J. Biol. Chem. 258(3): 1450–1455 1983.

Primary Examiner—William H. Beisner
Assistant Examiner—Nancy J. Degen
Attorney, Agent, or Firm—Wenderoth, Lind & Ponack

[57] ABSTRACT

A self-supporting composite bioactive material and method of making it, which comprises immersing a body of collagen in a solution comprising a calcium phosphate and a phosphoprotein (preferably containing o-phosphoserine residues) to deposit on the collagen a mineralized layer of calcium phosphate and the phosphoprotein.

7 Claims, 2 Drawing Sheets

Fig.1.          200μm
Fig.2.          200μm

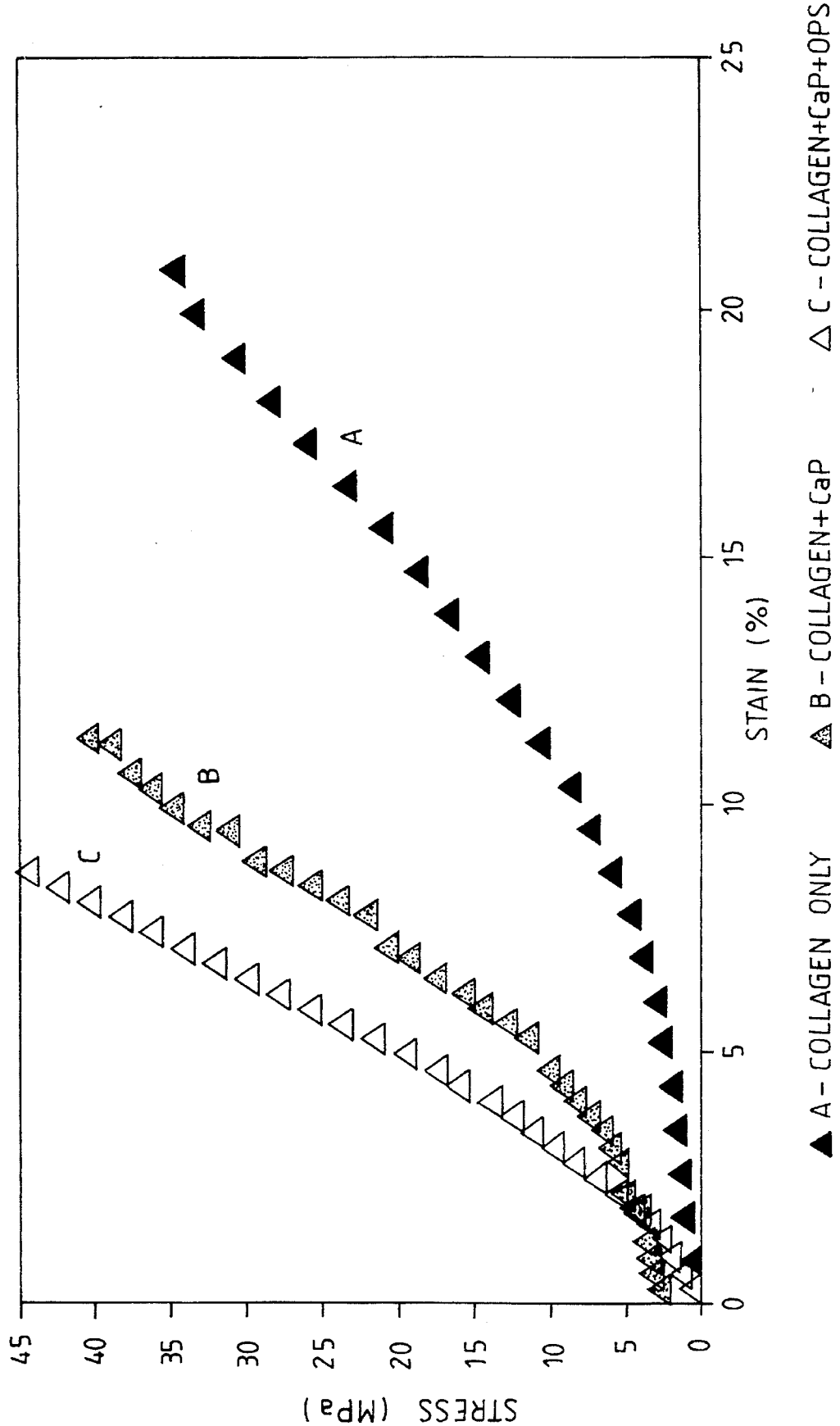

BIOACTIVE MATERIAL

A material that does not produce adverse biological side effects when placed in the body is termed a biomaterial, and as such is classified as either bioinert or bioactive. Osteogenic bioactive materials stimulate bone regrowth, and are generally composed of natural materials. Implants of porous hydroxyapatite[1], collagen combined with gelatin[2], and hydroxyapatite immersed in a collagen gel[3] have all shown excellent bone regenerative capacity, but unfortunately have been unable to provide the mechanical properties for use as implants in stressed regions. Bioinert materials, on the other hand, have mechanical properties superior to the bioactive materials but are not recognised by the immune system, allowing no interaction with the living tissue causing the implant to remain permanently within the body.

Calcium phosphate may precipitate out of aqueous solution as: dicalcium phosphate dihydrate (Ca/P ratio 1:1); octacalcium phosphate (Ca/P ratio 1.33:1) and hydroxyapatite (Ca/P ratio 1:67:1). (An amorphous calcium phosphate, of variable composition, sometimes precipitates initially.) The thermodynamic factors governing the nucleation and growth of calcium phosphate phases on both hydroxyapatite seed crystals and reconstituted collagen have been studied extensively by Nancollas[4,5]. The involvement of kinetic factors has been investigated by Boistelle[6].

Glimcher[7] and Endo[8] have studied the effect of incorporating the amino acid residue o-Phosphoserine with collagen in the solid state prior to mineralisation and found that the lag-time occurring before mineral precipitation, decreased on adding the protein. The main distinctive feature of phosphoprotein is the presence of the residues of the phosphoserine amino ester unit. Many other experimenters have investigated the effect of proteins on mineralisation. Termine[9] found osteonectin to enhance the mineralisation process and suggested that it formed a "link" between collagen and mineral, whereas Doi's[10] experimentation deemed the same protein to inhibit mineralisation. Similar arguments have taken place over osteocalcin and osteopontin. Overall, the results of the effects of proteins on mineralisation are inconclusive due to conflicting information.

The mechanical properties of many different types of animal bone have been tested by Currey[11], giving Young's Modulus and Ultimate Tensile Strength (UTS) values of 2 to 50 GPa and 40 to 200 MPa respectively. Mechanical properties of any bioactive materials so far produced have not been extensively tested, but those of bioinert materials have been shown to be far superior to natural bone. Stress shielding resulting in bone resorption is one of the main reasons why these mechanical properties are not conducive to implant longevity. Therefore, a biomaterial with mechanical properties closely matched to those of bone, with bioactive capacity, is required to stimulate bone regrowth. The present invention provides such a material. Accordingly, the present invention provides a self supporting composite bioactive material comprising a collagen substrate carrying a layer comprising a phosphoprotein and calcium phosphate deposited from a solution comprising the phosphoprotein and calcium phosphate.

The invention further provides a method of making a self supporting composite bioactive material which method comprises immersing a body of collagen in a solution comprising calcium phosphate and phosphoprotein for a period sufficient to deposit on the collagen a mineralised layer of calcium phosphate and phosphoprotein.

The collagen substrate may be, for example, in the form of fibrils or collagen sheet. However, the collagen should be continuous i.e. not powder or particles, in order to obtain the necessary strength characteristics when mineralised. The collagen may be obtained from demineralised bone, although this is not necessary.

Over a range of conditions from acidic to slightly basic, and depending on the calcium ion concentration in solution, the calcium phosphate of the calcium phosphate/phosphoprotein layer is generally formed as dicalcium phosphate dihydrate (Ca/P ratio=2:1). The hydroxyapatite characteristic of bone has a characteristic Ca/P ratio of 1.67:1. However, if desired the phase of calcium phosphate can be changed following deposition by techniques well known to those skilled in the art.

The phosphoprotein, or active part thereof, used may be any phosphoprotein which is able to bind to collagen and act as a nucleation site for calcium phosphate deposition, although bone specific phosphoproteins or amino acid residues such as o-Phosphoserine are preferred.

In the preparation of the material a body of collagen is immersed in a mixed hydroxyapatite/phosphoprotein solution. The pH of the solution should preferably be from 4 to 8, particularly 4–6 or 5–6. The hydroxyapatite solution should preferably be at least 3 mM, most preferably about 50 mM or more. The overriding factor in the value of the calcium ion concentration is that the solution is supersaturated with respect to one or more of the calcium phosphate phases.

Whilst it is possible to deposit calcium phosphate crystals on collagen from hydroxyapatite solution without the use of a phosphoprotein the morphology of the crystals is different when a phosphoprotein is used. Without o-phosphoserine platelike crystals are formed but with phosphoserine tight efflorescences of needlelike crystals are formed. The inventors believe that this latter morphology is necessary for useful properties of the composite. Similar behaviour is observed when the precipitating phase is octacalcium phosphate (Ca/P ratio 1.33:1).

The present inventors have found that whilst phosphoserine is necessary for the formation of a mineral layer of appropriate morphology, too high a concentration will reduce the degree of mineralisation and not produce a satisfactory composite.

For phosphoserine, the concentration in solution should be less than 10 mM, preferably 0.5–5 mM or less. The exact concentration may vary for different phosphoproteins but the appropriate concentration can be readily determined by observing the morphology and density of the calcium phosphate crystals.

The inventors believe that the phosphoprotein may be complexing with free $Ca^{2+}$ ion and if too much is added total complexing of $Ca^{2+}$ occurs and no free ions are available for crystal growth. Thus, a concentration of phosphoprotein should be used which provides crystal of the appropriate morphology but does not complex all $Ca^{2+}$ ions.

The present material has potential for use as a bone filler in orthopaedic techniques. The collagen substrate can be moulded to any shape desired prior to mineralisation. The mineralised article is self supporting has physical and mechanical properties similar to that of natural bone. It is thus able to function mechanically like normal bone when inserted, unlike presently available plastic materials which are presently used but which are not mechanically stable. Neither does this material have mechanical properties which are so much greater than bone that they lead stress shielding and bone resorption.

As well as having mechanical properties closely matched to bone, the present material is physically and chemically similar to natural bone. This means that there is little problem with rejection by the body and in fact the present material is bioactive in that it promotes bone regeneration and new bone tissue is found to grow rapidly through the present material. The rate of growth is in fact found to be more rapid than seen with natural bone, which is sometimes used in order to encourage new growth.

BRIEF DESCRIPTION OF THE DRAWINGS

Reference is directed to the accompanying drawings:

FIG. 1—A scanning electron micrograph showing plate-like crystals of dicalcium phosphate dihydrate grown on decalcified bone.

FIG. 2—A scanning electron micrograph showing the smaller needlelike efflorescences of dicalcium phosphate dihydrate grown on decalcified bone with the addition of 1 mM O-Phosphoserine.

FIG. 3—Stress-strain curves of the prepared tensile specimens (crosshead speed 1 mm/min).

The present invention will now be illustrated in the following examples.

EXAMPLE 1

The material was prepared by immersing decalcified bone, obtained from rabbit femur by EDTA extraction, in a 50 mM hydroxyapatite solution at pH 5.5. Small samples of decalcified bone (10×10×1 mm) were let in 40 ml solution for 5 days before examination in a Scanning Electron Microscope. A large piece (5×20×1 mm), for use as a tensile test specimen, was mineralised in two separate identical solutions each for ten days consecutively, before being dried in a desiccator overnight. These two experiments were repeated using the mineralising solution with additions of 1 mM and 10 mM O-Phosphoserine (OPS), a bone specific phosphoprotein found at initial mineralisation sites in bones. The tensile specimens were tested on Instron 1195 in the wet condition, having been immersed overnight in their respective mineralising solutions. Also, a tensile test specimen of unmineralised decalcified bone was prepared and tested wet. The Young's Modulus and UTS were recorded. The wt % mineral contained in the tensile specimens was determined by heating to 800° C. in a furnace after testing, when the organic component burnt off and the mineral left could be measured as a percentage of the total weight.

Platelike crystals of dicalcium phosphate dihydrate (DCPD) (100×30 μm) were deposited from the standard mineralising solutions with no protein present (FIG. 1), which was verified by using a Cameca Microprobe to measure the Ca/P ratio of the crystals. On addition of OPS, morphology of the crystals changed to give tight efflorescences of small needlelike crystals (FIG. 2), and also surface coverage of mineral increased by a factor of three as the number of nucleation sites increased. However, when 10 mM OPS was added, the surface cover of mineral decreased drastically to only 5%, but the efflorescent morphology was unchanged. The phase of the crystals does not change on addition of the OPS. These results indicate that the presence of OPS is influencing the mineralisation process, most probably by complexing with the free $Ca^{2+}$ ions, and forming a bridge between the collagen and the mineral as postulated by Glimcher[7], making use of the charged groups that exist on the amino acid molecule in solution. This would explain the increase in the surface coverage of the substrate.

Also, if too much OPS is present (as in the 10 mM experiment), total complexing may occur and little or no free $Ca^{2+}$ ions are available for mineral growth.

The stress-strain curves of the various samples tested are shown in FIG. 3. As mineralisation proceeds the modulus increases from 344.8 MPa for the collagen alone, to 513.2 MPa and 698.4 MPa for decalcified bone mineralised without (contains 9.1 wt % mineral after mineralisation) and with OPS (contains 13.1 wt % mineral after mineralisation) additions respectively, representing an overall modulus increase of 100%. The UTS also increased by approximately 40% from 34.66 MPa to 44.87 MPa on mineralisation and then further increased to 45.83 MPa on addition of OPS to the mineralising solution. It can be seen that the strain to failure decreases as the strength increases. The fracture surfaces of unmineralised and remineralised tensile specimen were examined. The osteons were visible in the unmineralised case, but after mineralisation the mineral was seen in the interior of the sample, obscuring the osteons and demonstrating that this growth technique produces mineral through the cross-section for the sample, and not just on the surface. The fracture surface appeared more brittle after remineralisation and as the strain to failure is also lower, the crystalline content of the material must be affecting the energy absorption mechanisms in operation. The general shape of the stress/strain curves is typical of a soft and tough elastomer, exhibiting rubberlike elasticity, although at relatively low elongations due to the complexity of the collagen molecule. The increase in modulus is due to the incorporation of the mineral phase and as such a simple composite law of mixtures can be applied[12]. This is, of course, dependent on the position of the calcium phosphate crystals in relation to the collagen fibrils. The strengthening may be attributed to a variety of mechanisms, such as the extra energy requirement of breaking the collagen-mineral bonds to allow collagen fibre pull-out or extension.

EXAMPLE 2

The bioactivity of this material was assessed by co-culturing with human-derived bone cells and examining the effects histologically. The cells were obtained by outgrowth from normal human trabecular bone using the method described by Beresford et al[11]. The test material was cut into fragments of 6×3 mm and sterilised using ethylene oxide for 30 minutes. Single fragments were then added to the wells of a 24-well multiwell culture plate with 1 ml of culture medium. The culture medium used was Dulbeccos modification of Eagles minimum essential medium supplemented with 10% (v/v) heat-inactivated foetal calf serum, 2 mM L-glutamine, 20 mM HEPES, 100 μM L-ascorbic acid 2-phosphate, 100 units/ml benzyl penicillin and 100 μg/ml of streptomycin. The cells were added at a density of $2.4 \times 10^4$ cells/well and incubated at 37° C. in an atmosphere of 5% $CO_2$ and 95% humidity. The medium was changed every 2 days.

After 32 days, the material fragments were removed and fixed in 95% methanol at 4° C. and embedded in methacrylate. Sections were cut for light microscopy and stained with toluidine blue and Von Kossa stains, or with toluidine blue alone. The Von Kossa stain, specific for phosphate, showed a phosphate gradient with higher amounts of phosphate close to the surface of the fragment but also penetrating well into the fragment in some areas. The bone-derived cells had adhered to the fragment and produced a substantial amount of matrix which had mineralised in some areas. Cells adjacent to the fragment surface had taken on a plump cuboidal appearance which is typical of active osteoblasts found on bone surfaces in vivo. At the periphery the cells were fibroblastic in nature and had formed a loose connective tissue. Between these two areas there was a dense matrix which has the appearance of newly formed osteoid. This differentiation pattern had a spatial relationship to the fragment, indicating that this material had promoted osteoblastic differentiation.

EXAMPLE 3

Several collagen sheets, approximately 20 μm thick (used as a haemostat), were mineralised using the method of the invention. These were pressed together and further mineralised for a total of 10 days to make discs up to 1 mm thick by 15 mm in diameter. Cube samples were cut from these discs and tested in compression. The following results were obtained from compression tests. Compressive strength>400 MPa, modulus,>2 GPa, strain to failure~50%. Samples 4 mm wide and 12 mm long were tested in tension. From pre-cracked samples the toughness was determined to be>1800 Jm$^{-2}$. The mechanical properties were highly anisotropic, because sheets are used. Thus, a suitable design of the way the material is laid up may be important, for example, spiralling the collagen sheets either before or after mineralisation or folding in a concertina fashion. This shape design would permit some control in tailoring the material to take into account the stress state in actual use. For collagen fibres similar considerations apply.

References

1. De With G., Corbijan A.J.; Journal of Materials Science, 24, pp 3411–3415, 1989.
2. Sugaya A., Minabe M., Tamura T., Hori T., Watanabe Y.; Journal of Periodontal Research, 24, pp 284–288, 1989.
3. Sasaki N., Umeda H., Okada S., Kojima R., Fukada A.; Biomaterials, 10, pp 129–132, 1989.
4. Nancollas G.H., Amjad Z., Koutsoukos, P.; American Chemical Society, 1979.
5. Nancollas G.H., Zwacki S.J.; Connective Tissue Research, 21, pp 239–246, 1989.
6. Biostelle R., Lopez-Valero I.; Journal of Crystal Growthg, 102, pp 609–617, 1990.
7. Glimcher M.J.; Philosophical Transactions of the Royal Society London B 304, pp 479–508, 1984.
8. Endo A. and Glimcher M.J.; Connective Tissue Research, 1989, Vol. 21, pp 179–196
9. Termine J.D., Kleinman H.K., Whitson S.W., Conn K.M., McGarvey M.L., Martin G.R.; Cell, 26, pp 99–105, 1981.
10. Doi Y., Okuda R., Takezawa Y., Shibata S., Moriwaki Y., Wakamatsu N., Shimizu N., Moriyaa K., Shimokawa H.; Calcified Tissue International, 44, pp 200–208, 1989.
11. Currey J.D.; Journal of Material Science, Materials in Medicine, 1, 00 14–20, 1990.
12. Beresford J.N., Gallagher J.A., Poser J.W., Russell R.G.G.; Metabolic Bone Disease and Related Research, 5, pp 229–234, 1984.

We claim:

1. A self supporting composite bioactive material comprising a collagen substrate carrying a layer comprising a phosphoprotein and calcium phosphate deposited from a solution comprising the phosphoprotein and calcium phosphate.

2. A self supporting composite bioactive material according to claim 1 wherein the phosphoprotein is a bone specific phosphoprotein.

3. A self supporting composite bioactive material according to claim 1 wherein the calcium phosphate has a Ca/P ratio of 2:1.

4. A method of making a self supporting composite bioactive material which method comprises immersing a body of collagen in a solution comprising calcium phosphate and phosphoprotein for a period sufficient to deposit on the collagen a mineralised layer of calcium phosphate and phosphoprotein.

5. A method according to claim 4 wherein the phosphoprotein is a bone specific phosphoprotein.

6. A method according to claim 4 wherein the phosphoprotein contains phosphoserine.

7. A method according to claim 4 wherein the phosphoprotein is present in the solution at a concentration of from 1 to 5 mM.

* * * * *